(12) United States Patent
Pierce

(10) Patent No.: US 6,357,066 B1
(45) Date of Patent: Mar. 19, 2002

(54) PATIENT SUPPORT DEVICE

(76) Inventor: Carla Terzian Pierce, 3361 Barranca Ct., San Luis Obispo, CA (US) 93401

( * ) Notice: Subject to any disclaimer, the term of this patent is extended or adjusted under 35 U.S.C. 154(b) by 0 days.

(21) Appl. No.: 09/505,104

(22) Filed: Feb. 16, 2000

(51) Int. Cl.⁷ .............................................. A47C 27/10
(52) U.S. Cl. ................... 5/710; 5/713; 5/727; 5/740; 5/731
(58) Field of Search ................... 128/869, 870, 128/876, 878; 5/710, 713, 731, 733, 740, 727, 730, 655.3, 655.9

(56) References Cited

U.S. PATENT DOCUMENTS

| 2,748,399 | A | * | 6/1956 | Rockoff | 5/710 |
| 3,700,229 | A | * | 10/1972 | Kurokawa et al. | 5/601 |
| 3,861,666 | A | * | 1/1975 | Nishiyama et al. | 5/601 |
| 4,489,452 | A | * | 12/1984 | Lickert | 5/710 |
| 4,688,283 | A | * | 8/1987 | Jacobson et al. | 5/731 |
| 4,791,687 | A | * | 12/1988 | Iwase | 5/731 |
| 4,805,603 | A | | 2/1989 | Cumberland | |
| 4,907,306 | A | | 3/1990 | Nakaji | |
| 5,613,254 | A | | 3/1997 | Clayman et al. | |
| 5,785,669 | A | * | 6/1998 | Proctor et al. | 5/655.3 |

* cited by examiner

Primary Examiner—Michael F. Trettel
(74) Attorney, Agent, or Firm—Pendorf & Cutliff

(57) ABSTRACT

A patient support device, and more particularly, a patient support device which provides improved full-body comfort to conscious patients immobilized for one or more hours while undergoing imaging or interventional procedures. The patient support device preferably comprises a foam for supporting the body and inflatable bladders for providing adjustable comfort to the cervical, lumbar and patellar regions of the patient. Arm restraints which safely and securely position patient's arms laterally on a narrow support (table).

20 Claims, 4 Drawing Sheets

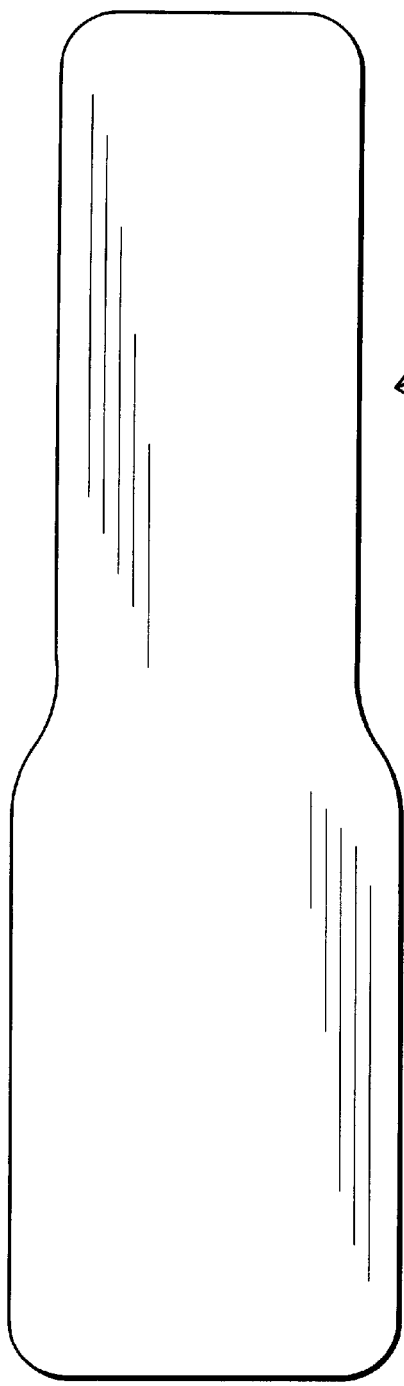
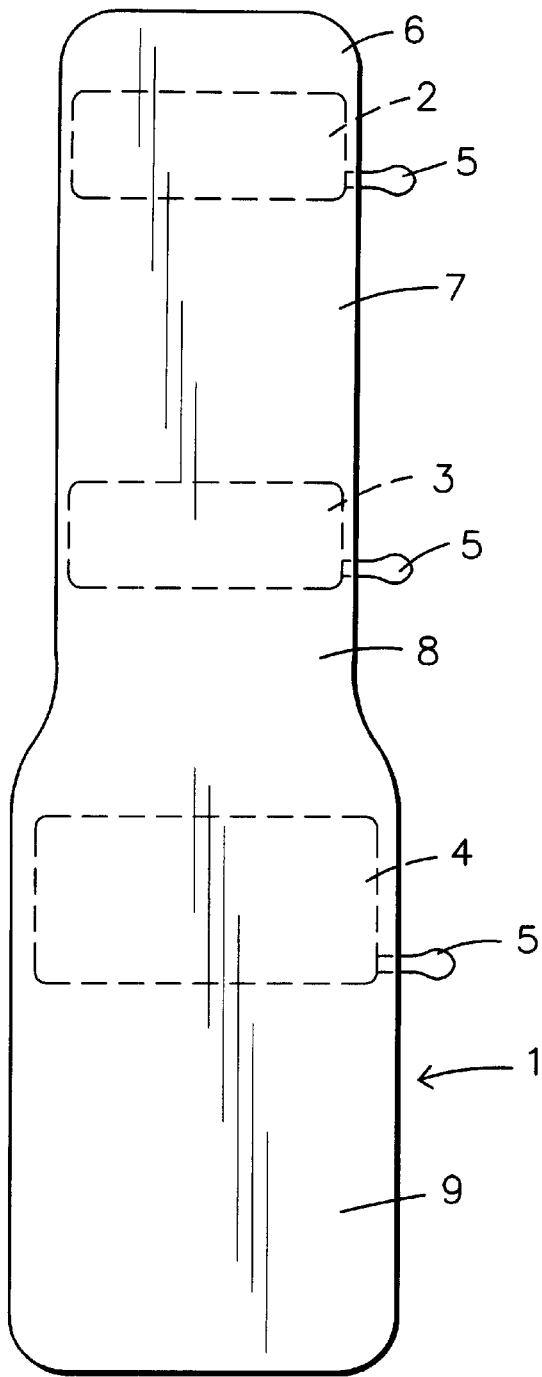
Fig. 1
Fig. 2

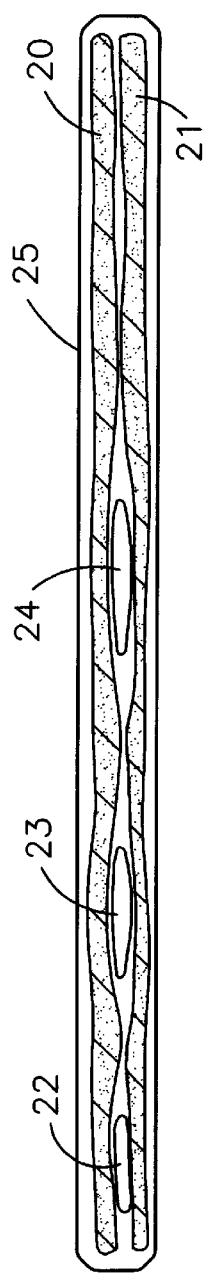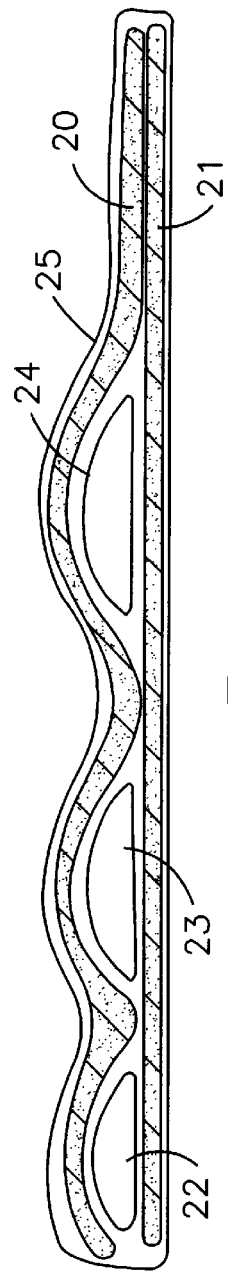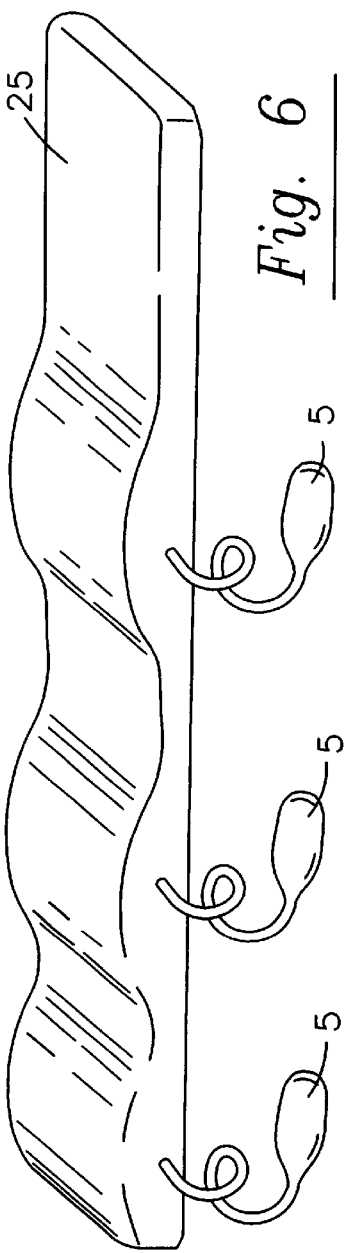

PATIENT SUPPORT DEVICE

BACKGROUND OF THE INVENTION

1. Field of the Invention

The present invention relates to a patient support device, and more particularly, to a patient support device which provides improved full-body comfort to alert patients immobilized for one or more hours while undergoing imaging or interventional procedures.

2. Description of the Related Art

An increasing demand for diagnostic and interventional services such as femoral catheterization and coronary angiography, coupled with an increase in the complexity of the procedures, has resulted in a turbulent environment.

In these procedures a conscious patient is voluntarily immobilized on a temporary patient support, usually a 1-inch thick vinyl-covered foam pad, for one or more hours while undergoing diagnostic scanning or interventional procedures. During these procedures cardiologists and/or radiologists focus on the patient's image/x-ray and the physicians focus on the procedure at hand. In the patient, lying still, anxious and alert, even a slight positional discomfort could, over a short time, develop into pain. The care/assessment and evaluation as well as the treatment of the patient is delegated to the nurse, who currently has limited resources for improving patient comfort.

The present inventor considered that if a baseline of patient comfort/satisfaction could be assured prior to the onset of any diagnostic or interventional procedure, the nurse could readily assess and treat the patient according to their actual physiologic symptoms (e.g., ischemic chest pain) instead of possible positional pain. Although the present inventor has felt a need for improving patient comfort prior to and during such procedures, there is no economical device or method for assuring patient full-body comfort.

The need for such a device or method increases with the increasing prevalence of procedures in which a conscious patient is required to lie immobile for one or more hours. For example, diagnostic and/or imaging procedures are normally performed outside the operating room, in a suite containing the scanning machine (CT, MRI, x-ray, etc.) and is dedicated to scanning procedures. During scanning, the patient is supported and moved about (translated or transferred) on a temporary support. Translation permits the patient to be moved into the scanning field of the scanning apparatus. Due to physical obstructions inherent in the bulky architecture of the scanning apparatus, particularly with MRI and CAT scans, the patient support is designed to be as narrow as possible, usually about 18 inches in width. The support is usually not wide enough to support the arms, and is narrowed in the area of the head.

The development of miniaturized surgical instruments and probes has resulted in an increase in the popularity of non-invasive surgery. Non-invasive surgery is usually performed using the above-mentioned imaging equipment as the eyes of the physician. The patient support is thus designed to be as narrow as possible to provide access not only to the surgical team, but also to the imaging equipment.

For example, carotid stenting is normally performed in the angiography room of the cath lab or x-ray department, and requires a conscious patient to remain immobile in a supine position for two hours or longer. A catheter is inserted into the patient's femoral artery through a small incision in the right or left groin area. The catheter is selectively positioned up the aorta to the neck region where the carotid artery is blocked. Every few moments contrast is injected through the catheter. Using X-ray equipment (fluoroscopy), the patient's blood vessels are continuously digitally imaged and monitored on overhead monitors, providing exact views by which the physician must guide or direct the catheter to reach the problem area.

Next, the physician inserts a second, more slender catheter inside the first one, with the stent over its tiny inflatable balloon stored securely inside crimped firmly to the catheter's end. The patient—already immobile for almost one hour—is then asked to lie perfectly still and to not even swallow for the next few minutes. The stent is positioned, the balloon inflated, and stent stretched open to form a tiny wire cage, supporting the lumen or walls of the vessel. During this procedure the blood flow to the brain is constantly monitored. The angiography X-ray unit is repositioned around the patient, taking digital (moving) images from different angles. To this point, the procedure has taken two hours, during which the patient has remained awake and largely motionless. Any discomfort experienced by the patient during this period grows and intensifies over time.

As another example, percutaneous translumenal coronary angioplasty (PTCA) involves the percutaneous introduction of an inflatable balloon tipped catheter assembly into the femoral artery and its advancement through the arterial system to, e.g., an atherosclerotic coronary lesion. The balloon is then inflated to dilate the constricted vessel followed by stent placement in most cases.

Yet another non-surgical technique, intra-aortic balloon pump (IABP) counterpulsation, provides circulatory assistance to a patient experiencing cardiogenic shock. Using a needle, a guide wire and a dilator sheath assembly, an elongated catheter-mounted balloon pump is inserted percutaneously through an introducer sheath into a femoral artery, and the assembly travels through the abdominal aorta towards the heart and is positioned into the descending thoracic aorta.

For procedures such as those discussed above, catheterization of the femoral artery (and more recently the radial or wrist artery) is performed in a catheterization lab separate from the operating room where the patient is conscious, and not under general anesthesia such as is generally the case in the surgical suite or operating room.

For both scanning and catheterization, the patient support is considered to be only a temporary support. The patient rests on a one inch thick, vinyl covered foam pad. Apparently, a thin foam pad is believed to increase the stability (decrease roll) of the patient during imaging, and is erroneously believed to give adequate support and comfort to the patient.

However, from the perspective of the patient, such a thin and planar foam pad does not sufficiently conform to the contours of the body and thus fails to provide sufficient support. The patient is asked to remain perfectly motionless on this thin and narrow pad for one or two hours, during which he is awake and able to verbalize any concerns. Patients commonly complain of positional discomfort including back, hip, shoulder and neck pain, often requiring administration of narcotics for pain control. This can be associated with additional risk to the patient and may lengthen the post procedure phase of their care (as well as increase the cost to both the patient and hospital). Any undesirable vovement may cause the procedure to lengthen due to poor imaging quality combined with the need to repeat images. This repetition is costly and time consuming, and causes increased risk to patient, staff and physician.

Further, since the narrow support does not provide for patient arm support, the hands of the patient are simply tucked under the hips to secure them by their sides. This awkward positioning of the arms and hands is one of the primary causes for the patient's discomfort and pain. Any minor discomfort, left unaddressed for as little as five or ten minutes, tends to intensify and develop into severe pain. Patient movement in response to the pain can be dangerous to the patient during a procedure as discussed above.

As discussed above, it is often the responsibility of the nurse to monitor and alleviate patient discomfort. This must be done without interfering with the imaging or interventional procedure at hand.

With the foregoing in mind, the present inventor investigated the presently available devices for supporting patients, and has found none which are simple in design, capable of use in conjunction with existing patient supports (gurneys, tables) and able to comfortably and safely support the full bodies of patients of varying body shapes and sizes.

A search of patent literature has revealed U.S. Pat. No. 5,742,963 entitled "Patient support apparatus" and teaching a patient support apparatus which includes a firm body support portion constructed of foam, with the foam having a first side for placement on a bed or gurney, and the second side upon which the body of the patient would be laid. The foam apparatus would include a principal upper torso support portion for supporting a patient generally from the top of the patient's head to the lower buttock region of the patient; first and second leg portions which are attachable to a lower edge of the principal body support portion for supporting the legs of the patient, and attachable arm portions secured to the side edges of the upper body support portion for accommodating the arms of the patient. The upper sides of the principal body portion, leg portions and arm portions would further include contoured regions which would reflect the general shape of the patient as the patient is laid on the patient's back on the apparatus, and would provide a soft yet firm support for the patient along the entire body region of the patient during transport. However, as the foam support is not adjustable, this "one size fits all" approach does not always provide satisfactory results.

U.S. Pat. No. 5,054,142 entitled "Contoured body cushion" teaches a portable multi-component contoured body cushion for supporting at least portions of a body includes a head member configured and dimensioned for supporting the head portion, a chest member configured and dimensioned for supporting the chest portion, and an abdomen member configured and dimensioned for supporting the abdomen. If desired, an ankle bolster configured and dimensioned for supporting the lower leg and ankle portions is also provided. The chest member is formed of a plurality of preformed sheets of uniform thickness configured so as to provide recesses to accommodate the breasts and abdomen of the body and to provide supports at least for the sternum and collar portions. The abdomen member is formed of a plurality of preformed sheets of uniform thickness positioned one atop the other. This abdomen member is also configured so as to provide support for the pelvic region so as to generally straighten the lumbar spinal curve. Since the members are pre-formed, they best support a "standard" figure.

U.S. Pat. No. 5,224,226 entitled "Body support structure" teaches a body support structure in the form of a mattress for supporting a person lying thereon. It comprises a body of resilient, compressible material, having a surface layer of resilient soft material. The body includes a head end edge and a foot end edge at its opposite end; two substantially parallel straight elongated side edges; a bottom face extending between the two side edges of the body; an upper face opposed to and spaced from the bottom face between the two side edges of the body; two spaced apart elongated ridges, one of the ridges extending along each side edge; a channel provided in the upper face extending between the two ridges, the channel joining smoothly to the two ridges on either side; a central raised part located in the channel between but distanced away from the opposite end edges and being positioned to support the lumbar region of a person lying in the channel and side parts provided on the ridges adjacent the central raised part. Again, this device is not adjustable in a simple manner to "dial in" optimal comfort of the patient.

Finally, U.S. Pat. No. 4,907,306 entitled "Supine support device and method for treatment and prevention of malocclusion of the teeth" teaches a wedge-shaped pillow having recessed areas for a user's torso and head to promote supine sleeping as a beneficial deterrent to orthodontic problems and to generally promote sleeping comfort. Detachable foam cushions may be provided in the lumbar and cervical regions. Removal and replacement of such foam cushions is inconvenient and time consuming, and worth-while only if the device is intended for use over a period of weeks or months. It would be inconvenient to adjust such a device to provide optimal comfort to single-use patients.

Not only are quality images and favorable therapeutic outcomes important, but also patient satisfaction is fundamental in the era of managed care. The patient must be satisfied with all aspects of the care he received. It is not enough that the patient "endured" a hospital stay—he must be left with a feeling of satisfaction. In addition procedural time will decrease if patient comfort, support and safe immobility is assured. The pain associated with long periods of conscious immobility—often during stressful procedures—must be mitigated.

Thus, there is a significant need for improvement in comfort when supporting a patient immobilized for even a brief time during imaging or interventional procedures. Obviously, from the perspective of the hospital it would be preferred if such improvement could be achieved without great expense, and with measurable improvement in patient satisfaction.

Further, since the support on which the patient rests is normally radiolucent, that is, transparent to the scanning device, so that the support does not compromise the utility of the scanned image, any modification to the temporary patient support must be fully radiolucent.

Further yet, given the large number of patients visiting an imaging or catheterization lab, expediency dictates that a patient support have a simple design, be intuitively easy to operate, and be carefree in servicing, maintenance and disinfection requirements. The greater the range of adjustment, the greater the risk of errors and problems.

SUMMARY OF THE INVENTION

The present inventor extensively investigated the positive and negative design features of patient supports in widespread use. The inventor particularly considered the need to alleviate the most common complaints of patients, the requirement to maneuver the patient support around and into imaging equipment, the reluctance of hospitals to buy completely new equipment, the need for the patient support to be fully radiolucent, and the need for the patient support to be simple in design and operation, so that patient satisfaction is easily and readily achieved.

After extensive experimentation the inventor discovered a simple device which:

can be used in conjunction with the existing patient supports in a "retrofit" manner, comfortably supports the body and prevents the major types of patient discomfort, is adjustable to the preferences of the individual patient, does not widen the patient support device and does not involve projections which may interfere with patient translation, allows for patient head restraint as indicated for cerebrovascular studies and interventions, allows for arm restraints for patient comfort and safe immobility, is fully radiolucent, can remain in place when not actively in use, is extremely simple in design and operation, and is easily disinfected.

More specifically, the inventor discovered that there are four specific areas of the conventional patient support which require improvement, and developed a simple device which addresses these areas.

The inventor determined that the uniformly flat one-inch foam pad upon which the body is resting for one to two hours is deficient in providing support in at three primary regions of the body necessary for the comfort of the patient, and determined that a significant improvement can be made by providing additional support means for selectively supporting one or more of the neck (cervical support), lower back (lumbar support), and knees (patellar support). In this regard, the inventive device comprises a patient support, preferably with integral foam pad, which can be simply laid over the top of a conventional foam pad, and/or which can be used as a replacement of the existing patient support pad, and which preferably comprises three inflatable bladders, one each for the cervical, lumbar and patellar areas. One or more additional bladders may be provided for comfort or immobilization of the head.

Further, the inventor determined that the arms of the patient in supine position can be simply and comfortably supported laterally along the sides of the patient using a modified pair of slings, i.e., flexible, waterproof and easily disinfected material, preferably vinyl, extending respectively laterally outward from the left and right sides of the supplemental support device, in the manner of wings. After the patient is positioned on the patient support device with arms placed along his or her sides, one sling is simply folded over the top of the patient with the tips releasably attached to each other using, e.g., VELCRO means at the patient's side. These slings are made of a radiolucent material, thus can be used in medical scanning without interference with the imaging process.

The foregoing has outlined rather broadly the more pertinent and important features of the present invention in order that the detailed description of the invention that follows may be better understood and so that the present contribution to the art can be more fully appreciated. Additional features of the invention will be described hereinafter, which form the subject of the claims of the invention. It should be appreciated by those skilled in the art that the conception and the specific embodiments disclosed may be readily utilized as a basis for modifying or designing other patient support devices for carrying out the same purposes of the present invention. It should also be realized by those skilled in the art that such equivalent structures do not depart from the spirit and scope of the invention as set forth in the appended claims.

BRIEF DESCRIPTION OF THE DRAWINGS

For a fuller understanding of the nature and objects of the present invention reference should be made by the following detailed description taken in with the accompanying drawings (not to scale) in which:

FIG. 1 is a top view of a conventional flat patient support pad.

FIG. 2 is a top view of a pad according to the invention, having the same outline as the pad of FIG. 1, and containing three bladders for comfort adjustment.

FIG. 4 is a side sectional view through the support pad of FIG. 2, with bladders deflated.

FIG. 5 corresponds to FIG. 4, with bladders inflated.

FIG. 6 is a side oblique elevated view of an inflated patient support according to the invention.

DETAILED DESCRIPTION OF THE INVENTION

Figure 3:
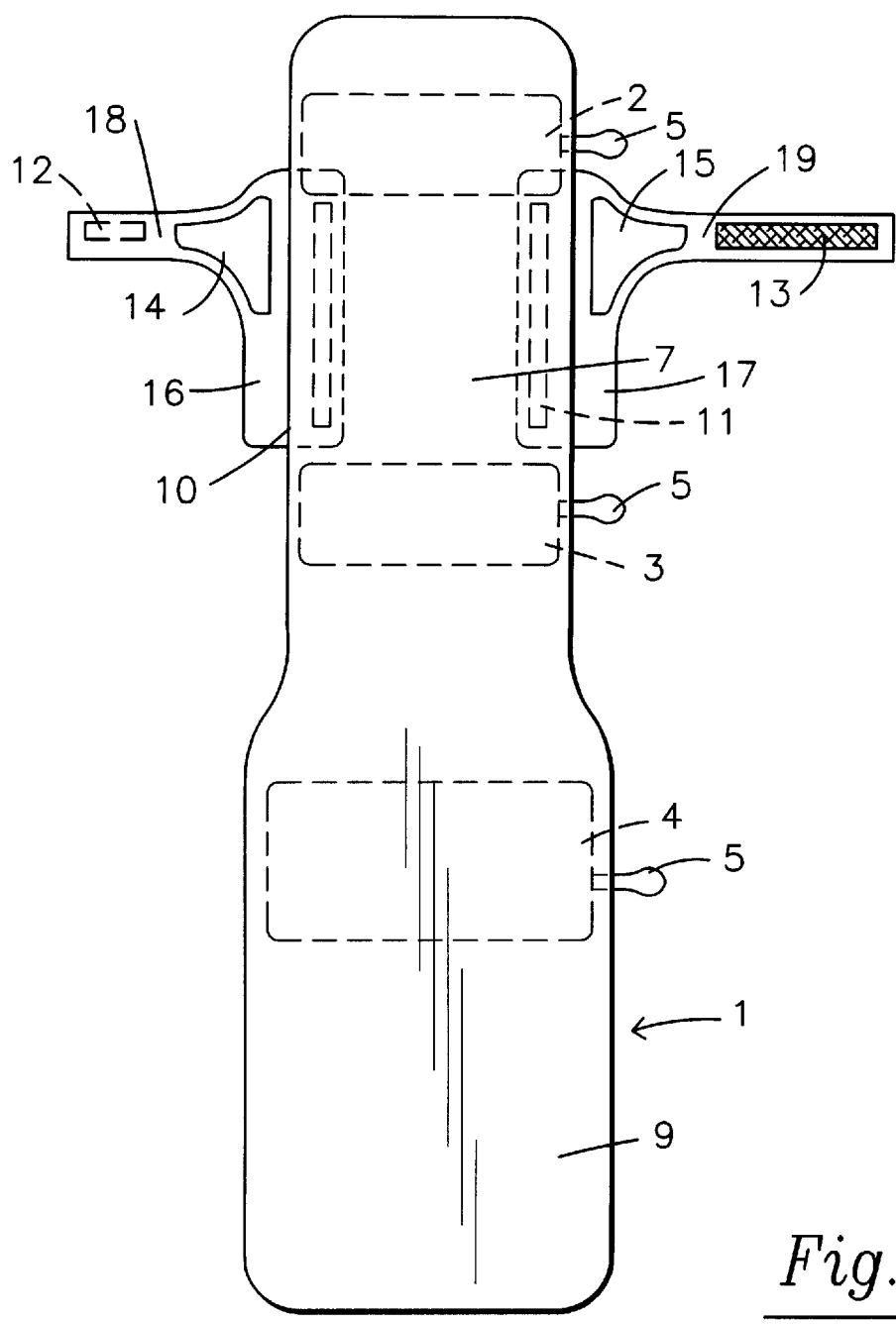
FIG. 3 is a top view of the patient support device as in FIG. 1, and further including slings for supporting arms along the patient's sides.

The inventive patient support device with inflatable bladders (hereinafter "pad") is uniquely designed to be either placed on top of a prior art patient support pad or to be used in place of a prior art support pad, and in either case providing much improved comfort in comparison to a conventional pad.

The dimensions of the pad vary according to shape of the rigid part of the patient support (hereinafter simply referred to as the "table"). The pad preferably has the same outline as the table top. In the illustrative embodiment, the device measures approximately 18" in width, 1" in depth (deflated) and 80" in length. It is slightly contoured, widening at the area below the patient's hips. This conforms with the standard catheterization lab tables and can also be utilized universally on all angiography tables with slight contour modifications for the head region (which is generally even narrower). Although these tables may vary slightly in their size and shape, they are considered by the patient—lying immobile for any period of time—to be hard, narrow and uncomfortable.

In a first embodiment of the invention, inflatable bladders for providing support in two or more supplemental support areas—that is, in the cervical, the lumbar, and preferably also the patellar regions—are incorporated into what is otherwise a conventional foam pad. The bladders are preferably sandwiched between upper and lower layers of foam, the foam serving to insulate the patient from any ridges or bumps due to hoses used for inflation and corners or edges of the bladders. The pad is covered with vinyl and—when not inflated—has the appearance of a conventional flat art pad.

In a second embodiment of the invention, a strap or sling is provided on each of the left and right sides of the patient support device. The slings may be permanently attached via stitching or adhesive, or may be removably attached via non-metallic hooks, snap fasteners or VELCRO. Removal of the slings from the pad facilitates repair or cleaning of the slings. However, it is envisioned that the slings will be made of durable vinyl, and thus will require little maintenance yet facilitate ease for disinfection.

Once informed of the basic concept of the present invention, it would be easy for those working in this art to construct working models of any of the various embodiments of the invention. Each of the materials and component elements of the invention are known in the art, can be selected to meet the particular demands of any consumer, and thus need not be described in great detail herein.

Inflatable air bladders are well known can be made of any flexible air-tight plastic or rubber material, and can be inflated using a conventional inflation means, such as a squeeze-bulb. Examples of suitable bladders can be found in U.S. Pat. Nos. 5,613,254; 5,016,268; 4,873,710; 5,679,040; and 5,647,079. Bladders may be any size and for the purposes of the present invention the three major bladders are about 9 by 17 inches, more or less depending upon the width of the pad.

Each bladder may have it's own associated hand or foot operated squeeze-bulb or similar device for inflation and deflation, or a single bulb may be selectively connected to one or more of multiple bladders via a manifold and control valve(s). Finally, it is also possible to connect the various bladders to a source of low-pressure air, as is readily available in hospitals. For example, the supply line to the inflatable bladders may be connected to the air source which is used for inflating the cuff of an automatic blood pressure measuring device. In a yet further alternative embodiment, a control unit may be provided remotely for controlling inflation of the bladders via low-pressure air. In this way, the comfort of a patient can be attended to remotely without disturbing the patient or requiring the attendant to approach the imaging equipment. In a preferred embodiment, using the manifold connected to a low-pressure air source, each bladder can be selectively inflated or closed off, and includes an overflow valve, (as is conventional in scuba diving personal floatation devices) such that air pressure will be able to escape without fear of over-inflation of the bladder.

It is even possible for the patient to have control over the inflation of the bladder(s). This can be done in an automated manner wherein the patient is provided with an inflate/deflate control switch, or in the manner of the inflatable flexible bladder mounted on the surface of a weightlifter's bench to provide support to the spinal region as taught in U.S. Pat. No. 5,304,109 entitled "Inflatable support". A pressure device activatable by the hand or foot of the weightlifter is employed to provide desired supporting internal pressure to the bladder. In this way the patient may himself immediately inflate or deflate one or more of the bladder(s) to his optimal comfort during the procedure without having to call upon a technician, and without having to wait for pain to develop.

Turning now to the foam material used in the pad, the material may be a foamed rubber (e.g., foamed neoprene, polyurethane, or polyethylene, preferably cross-linked polyethylene), or foamed plastic (e.g., foamed urea-formaldehyde, foamed polyvinyl-formaldehyde plastic, polyester resin reacted with aromatic diisocyanates to form a prepolymer which is then reacted with water to form a plastic urethane polymer which is foamed by coevolved carbon dioxide, phenolformaldehyde resin foams, and polystyrene), natural sponge, or any other such natural or synthetic material known to those in the art to have good stability, elasticity, and biocompatibility. The density of the foam layer may vary widely depending upon preferences, but is preferably about 4–6 lbs. per cubic foot, most preferably about 5 lbs. per cubic foot. The pad is preferably sized to provide a total thickness of about ¾ to 2 inches of contoured lift, most preferably about 1 inch. A pad thicker than 2 inch does not provide significant additional comfort, yet increases manufacturing cost. A pad less than ¾ inch in thickness is reduced in the amount of comfort afforded. A pad less than ½ of an inch is preferably used only in conjunction with (i.e., on top of) a prior art patient support pad having no inflatable bladders.

The foam material is covered with a material to improve wear resistance. This material is preferably a vinyl material to improve ease of cleaning and disinfecting. Alternatively, the pad may be covered with a breathable fabric such as cotton, nylon, polyester (e.g., DACRON, TERYLENE, or VYCRON), or polypropylene knit. The cover may be laminated to the foam material.

The bladders can be provided in the foam material in any desired manner. The bladders may be form-fittingly retained in pockets in the foam. The bladders at the lateral edge can even be introduced in VELCRO-closeable pockets, in the manner of pillows inside pillowcases, such that the bladders can be removed for repair. However, modern bladders have sufficient durability that no repairs of the bladder should ever be required. When inflated, the bladders preferably provide an additional 1 to 3 inches of lift or support.

In a preferred embodiment of the invention, the pad is constructed in a sandwich-like manner. Three inflatable bladders are positioned between half-inch (or even one-inch) thick, eighty inch long lower and upper sheets of foam material, preferably at 5–15 inches from the top for the head, 25–35 inches from the top for the lumbar support, and 46–56 inches from the top for the patellar support. Fabric receptacles can be incorporated between the foam pads for ease of introduction and removal of the bladders, in a pillow-case like manner.

The sheets of foam material preferably have slight depressions in the area of contact with the bladders, so that the "sandwich" has an even one (or two) inch thickness. This sandwich is then covered with the wear-resistant cover, with accommodation for air hoses used to connect the squeeze bulbs or other inflation means with the bladders.

As discussed above, the narrow support does not provide for patient arm support, and conventionally the hands of the patient are simply tucked under the hips to secure them by their sides. This awkward positioning of the arms and hands is one of the primary causes for the patient's discomfort, pain and inadvertent and untimely (as well as costly) patient movement. Arm support slings are a unique and especially useful adjunct to the patient support device. In a preferred embodiment of the invention, the pad of the present invention is provided with slings extending out from the left and right sides of the pad, in the manner of wings, the tips of which can be crossed over the body of the patient and releasably connected to each other at the side thereby cradling and supporting the arms against the sides of the patient. The arms of the patient are thus supplementally supported by the slings which serve, first, to keep the arms against the body and to prevent the arms from falling off the pad, and second, to cradle and support the arms.

The slings are preferably made of the same material as the material which is used to cover the foam pad. The slings may be provided with supplemental padding for improved comfort, but generally little or no padding is required. Thinner slings are preferred in order to keep the patient silhouette as small as possible. The slings may be releasably attached to the top or bottom of the pad using releasable fastening means such as plastic snap fasteners, radiolucent buttons, or VELCRO. The slings may be permanently joined to the pad by application of heat and pressure, such as by a flame lamination technique where an open flame is directed to the vinyl material. The open flame generates sufficient heat on the material surface to cause melting of the flat sheet of foamed material. Once melted, the sling layer is joined to the pad cover material and the laminate is preferably run between chill rollers under sufficient pressure that the sling and pad are permanently joined. Alternatively, an adhesive such as an epoxy or a chlorine based adhesive may be used to adhere the sling to the pad. Further yet, a breathable fabric can be sewn to the pad.

The slings are dimensioned to provide optimal support to the patient's arms while recumbent on the patient support device. The entire arm, from below the shoulder to above the wrist, is safely and securely held by the patient's side. The slings are generally triangular or funnel shaped, one being shorter with the distal edge at the patient's side. Distally the sling narrows into straps of about one or two inches in width which cross over the chest (above the abdomen) to allow access to the hip and abdominal area, yet does not interfere with cardiac imaging. As the patient is prepped for the procedure the nurse or technician is then assured that the patient's arms are tucked comfortably (and safely) by their sides. The arm support slings are secured to each other with VELCRO, off center toward the side of the patient, facilitating easy adjustment and release from the side of the patient if indicated, for example, during emergency resuscitation.

Another uniquely innovative characteristic of the arm support slings is they can be used for patients lying prone. This is a very important adjunct to the patient support device. Some procedures (for example, percutaneous nephrostomy tube insertions, or venous revascularization procedures for lower extremity thrombus) in the radiology suite require that patients be prone on the patient support table. This position mandates that either the arms be raised and tucked up under the patient's head, or just left to dangle from the sides without support. The arm support slings of the invention can be used as arm rest pads for supporting the prone patient's arms underneath the narrowed head of the table. The "modified sling" is easily formed in the following manner: The two slings are removed from the under-sides of the patient support device and then connected to each other at their base. The cushioned base is placed below the head of the table while the "chest straps" encircle the table on either side and attach up under the patient's head/pillow. The prone patient can then easily slide his/her arms into the "modified sling" just below the head. The size and position of the arm rest pad can easily be altered by adjusting the straps.

In a yet further variation of the invention, a tomography head restraint as disclosed in, e.g., U.S. Pat. Nos. 5,311,882 and 4,400,820 may be releasably attached to the patient support pad. The head restraint may comprise a one, two or three part cover, each part enclosing a pneumatic, inflatable member, adjustably assembled so as to locate each inflatable member around the patient's head. A strap encircles the forehead, maintaining the restraint on the patient. A hand held squeeze bulb simultaneously and equally pressurizes inflatable members so as to occupy all space between the patient's head and a U-shaped head holder typically not provided with tomography X-ray machines. The inflatable member(s) establish a comfortable fitting, flexible, large patch of contact with the patient's head and with the head holder. These characteristics immobilize a patient's head sufficiently to enable clear images to be developed. The inflated members are depressurized by a manual valve, and the restraint is readily removed from the patient.

Alternatively, a head restraint can be comprised of a less ample bladder system, in combination with a simple thin (optionally slightly padded) VELCRO strap that attaches to one side of the pad under the patient's head, runs over the forehead, and is VELCRO attached to the pad on the other side of the patient's head, preferably with some raising or bowing of the pad under the patient's head, thus immobilizing the head while providing comfort and support. This design is simple, unobtrusive, and easy to maintain and clean.

The design and manner of use of the improved patient support device of the present invention will now be described in greater detail on the basis of the drawings.

FIG. 1 is a top view of a conventional patient support device, of which only the foam pad 1, which has the same shape and dimensions as the underlying rigid support or "table", is visible.

FIG. 2 shows a patient support device similar to that shown in FIG. 1, but further including three bladders for providing an inflatable cervical support 2, lumbar support 3, and patellar support 4. The bladders are embedded within a foam material about 80 inches in length upon which the patient lies, and which includes an area for support of the head 6, upper back 7, buttocks 8, and lower legs 9. Each bladder is inflatable by hand using a squeeze-bulb 5. Each squeeze bulb includes a pressure relief valve for reducing pressure or evacuating the air bladder.

The supplemental patient support shown in FIG. 2 is simple to use. The patient reclines on the pad in the normal manner, with his head supported by the top of the patient support device and feet by the bottom. The cervical support 2 is inflated or deflated as necessary to provide the optimal support for the neck, the lumbar support 3 for supporting the lower back, and the patellar support 4 for supporting the region of the knees. The three bladders are individually deflated or inflated using the squeeze-pump 5.

Turning now to FIG. 3, the pad is provided with right and left slings 18, 19. As before, the patient is asked to lay on his back on the patient support in the normal manner. Air bladders 2, 3, 4 are adjusted for optimal comfort of the patient. The patient is asked to place his arms at his sides, and a right or left sling 18, 19 is folded over the patient's lower rib area and attached to the patient's opposite side or fastened to the opposite sling using VELCRO patches 12, 13, eliminating excess material in the imaging field. Optional shoulder pads 14, 15 of about ¼ inch thickness provide additional comfort to the patient. The lower parts of the slings 16, 17, when the slings are folded over the body, form semi-cylindrical cradles in which the arms rest and are retained at the sides of the patient. Due to the design of the slings, there is very little pressure on the chest, and they do not detract from coronary/thoracic imaging.

As the slings 18, 19 comfortably support the arms without adding any width to the patient support device and without interfering with the scanning or imaging process, they can be used in any diagnostic, imaging or interventional lab. The slings are extremely helpful in assuring proper patient positioning during an angiogram/intervention.

Preliminary tests have clearly demonstrated that the patient support device of the invention helps to relax and reassure the patient, and eliminates the common causes of discomfort associated with imaging or pre-surgical procedures carried out on a temporary patient support device over a period of one to two hours. Alternatively, if the patient indicates discomfort during the procedure, it has been demonstrated that by elevating one or more of the cervical, lumbar, and patellar zones with a few inflations (strokes of the hand pump) of the air bladders, the patient's response to pain relief can be expedient, thereby assuring patient satisfaction.

FIG. 4 is a side sectional view through the support pad of FIG. 2, with bladders deflated, and showing the "sandwich" structure of the device. Upper 20 and lower 21 foam pads of about one-half inch thicknesses are provided with slight exculpations or recesses in the surface areas contacting the cervical support bladder 22, lumbar support bladder 23, and patellar support bladder 24. The sandwich structure is surrounded by a vinyl cover 25, which is easily disinfected.

FIG. 5 corresponds to FIG. 4, with bladders inflated. The inflation is shown in exaggerated manner for illustrative purposes.

FIG. 6 is a side oblique elevated view of an inflated patient support according to the invention, without arm supports.

Figure 7:
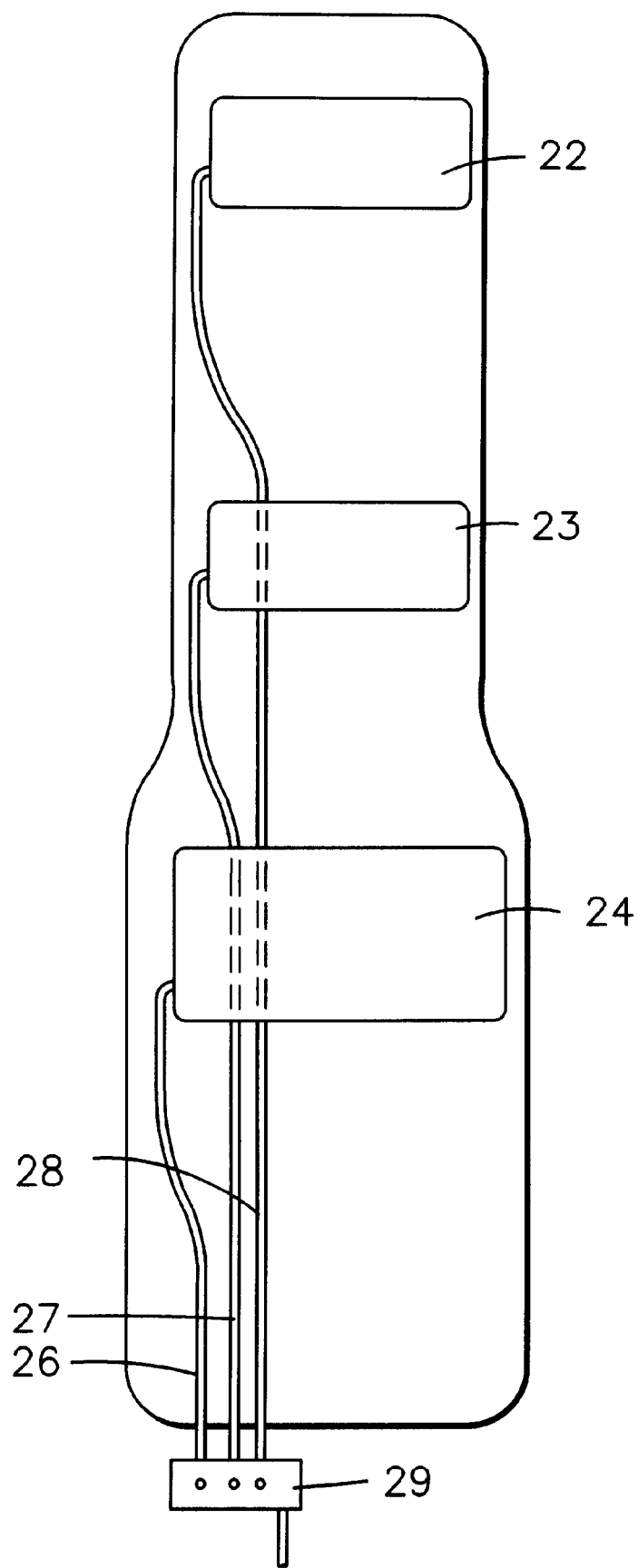
FIG. 7 is a top view of a patient support device wherein a single hand pump is connected through a three-valve manifold for selective inflation of bladders.

FIG. 7 is a top view of a patient support device wherein a single hand pump 5 is connected through a three-valve manifold 29 for selective inflation of bladders. Each bladder 24, 25, 26 is connected to the manifold 29 via an air hose 26, 27, 28. By selective opening and closing the valves of the manifold, the bladders can be individually or multiply accessed for inflation or deflation.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

Now that the invention has been described,
What is claimed is:

1. A patient full-body support device comprising:
    a foam pad for supporting the head, torso and legs of a patient;
    a selectively inflatable cervical air bladder incorporated in said foam pad for providing an adjustable level of support in the cervical region of the patient,
    a selectively inflatable lumbar air bladder incorporated in said foam pad for providing an adjustable level of support in the lumbar region of the patient,
    a selectively inflatable patellar air bladder incorporated in said foam pad for providing an adjustable level of support in the patellar region of the patient, and
    means for selectively independently inflating and deflating each of said cervical, lumbar and patellar air bladders.

2. A patient support device as in claim 1,
    wherein said foam pad has a top end and a bottom end and is from 70 to 85 inches in length, has a longitudinal axis, and is 15 to 25 inches in width,
    wherein said air bladder for providing support in the cervical region of the patient is from 8–15 inches by 5–15 inches deflated, extends transverse to the longitudinal axis of said pad, and is centered anywhere between 7 to 12 inches from said top end of said pad.

3. A patient support device as in claim 1,
    wherein said foam pad has a top end and a bottom end and is from 70 to 85 inches in length, has a longitudinal axis, and is 15 to 25 inches in width,
    wherein said air bladder for providing support in the lumbar region of the patient is from 10–24 inches by 5–15 inches deflated, extends transverse to the longitudinal axis of said pad, and is centered anywhere between 25 to 35 inches from said top end of said pad.

4. A patient support device as in claim 1,
    wherein said foam pad has a top end and a bottom end and is from 70 to 85 inches in length, has a longitudinal axis, and is 15 to 25 inches in width,
    wherein said air bladder for providing support in the patellar region of the patient is from 10–24 inches by 5–15 inches deflated, extends transverse to the longitudinal axis of said pad, and is centered anywhere between 45 to 60 inches from said top end of said pad.

5. A patient full-body support device comprising:
    a foam pad for supporting the head, torso and legs of a patient;
    a selectively inflatable cervical air bladder incorporated in said foam pad for providing an adjustable level of support in the cervical region of the patient;
    a selectively inflatable lumbar air bladder incorporated in said foam pad for providing an adjustable level of support in the lumbar region of the patient;
    a selectively inflatable patellar air bladder incorporated in said foam pad for providing an adjustable level of support in the patellar region of the patient; and
    means for selectively independently inflating and deflating each of said cervical, lumbar and patellar air bladders,
    wherein said bladders are removably introduced into pockets in said pad.

6. A patient support as in claim 5, wherein said pockets are made by separating said pad into upper and lower layers at least in the area of said pads.

7. A patient support as in claim 5, wherein said pockets are lined in fabric.

8. A patient full-body support device comprising:
    a foam pad for supporting the head, torso and legs of a patient;
    a selectively inflatable cervical air bladder incorporated in said foam pad for providing an adjustable level of support in the cervical region of the patient;
    a selectively inflatable lumbar air bladder incorporated in said foam pad for providing an adjustable level of support in the lumbar region of the patient;
    a selectively inflatable patellar air bladder incorporated in said foam pad for providing an adjustable level of support in the patellar region of the patient; and
    means for selectively independently inflating and deflating each of said cervical, lumbar and patellar air bladders,
    wherein said foam pad is comprised of upper and lower pads of approximately equal thickness and outline.

9. A patient support device as in claim 1, wherein said means for inflating and deflating one or more of said bladders comprises a conduit communicating with said bladder and a hand or foot operated air pump connected to said conduit.

10. A patient support device as in claim 1, wherein said means for inflating and deflating one or more of said bladders comprises a conduit communicating with said bladder and a source of low pressure air in communication with said conduit.

11. A patient support device as in claim 1, wherein said pad is covered with vinyl.

12. A patient full-body support device comprising:
a foam pad for supporting the head, torso and legs of a patient;
a selectively inflatable cervical air bladder incorporated in said foam pad for providing an adjustable level of support in the cervical region of the patient,
a selectively inflatable lumbar air bladder incorporated in said foam pad for providing an adjustable level of support in the lumbar region of the patient,
a selectively inflatable patellar air bladder incorporated in said foam pad for providing an adjustable level of support in the patellar region of the patient, and
means for selectively independently inflating and deflating each of said cervical, lumbar and patellar air bladders,
further including left and right slings, each sling having a base and a tip, wherein said bases are attached to said left and right sides of said pad, and wherein said tips are adapted for releasable attachment to each other.

13. A patient support device as in claim 12, wherein said slings are made of vinyl.

14. A patient full-body support device comprising:
a foam pad for supporting the head, torso and legs of a patient;
a selectively inflatable cervical air bladder incorporated in said foam pad for providing an adjustable level of support in the cervical region of the patient,
a selectively inflatable lumbar air bladder incorporated in said foam pad for providing an adjustable level of support in the lumbar region of the patient,
a selectively inflatable patellar air bladder incorporated in said foam pad for providing an adjustable level of support in the patellar region of the patient, and
means for selectively independently inflating and deflating each of said cervical, lumbar and patellar air bladders,
further including one or more additional bladders for supporting the head of the patient.

15. A patient support device as in claim 1, wherein said bladders are in communication with a single manifold for selectively directing air pressure to said bladders.

16. A patient full-body support device comprising:
a foam pad for supporting the head, torso and legs of a patient;
a selectively inflatable cervical air bladder incorporated in said foam pad for providing an adjustable level of support in the cervical region of the patient;
a selectively inflatable lumbar air bladder incorporated in said foam pad for providing an adjustable level of support in the lumbar region of the patient;
a selectively inflatable patellar air bladder incorporated in said foam pad for providing an adjustable level of support in the patellar region of the patient; and
means for selectively independently inflating and deflating each of said cervical, lumbar and patellar air bladders,
wherein said bladders are in communication with a single manifold for selectively directing air pressure to said bladders, and
wherein said manifold has an inlet and multiple outlets, wherein each outlet is connected to one of said bladders, and wherein said manifold has one valve associated with each outlet.

17. A patient support device as in claim 16, wherein said inlet is connected to a hand or foot air pump.

18. A patient support device as in claim 16, wherein said inlet is connected to a source of compressed air.

19. A patient support device as in claim 1, further including a strip of flexible material connected to said left and right sides of said pad and adapted for passing over the forehead of a patient to immobilize said head.

20. A patient full-body support device comprising:
first and second superposed foam pads of 70 to 85 inches in length for supporting the head, torso and legs of a patient;
a selectively inflatable air bladder incorporated between said first and second foam pads for providing an adjustable level of support in the cervical region of the patient,
a selectively inflatable air bladder incorporated between said first and second foam pads for providing an adjustable level of support in the lumbar region of the patient,
a selectively inflatable air bladder incorporated between said first and second foam pads for providing an adjustable level of support in the patellar region of the patient, and means for selectively inflating and deflating said air bladders,
wherein each of said bladders extends longitudinally over no less than 5 and no more than 15 inches.

* * * * *